(12) United States Patent
Gerke et al.

(10) Patent No.: US 10,053,412 B2
(45) Date of Patent: Aug. 21, 2018

US010053412B2

(54) PHOTOLABILE PRO-FRAGRANCES

(71) Applicant: Henkel AG & Co. KGaA, Duesseldorf (DE)

(72) Inventors: Thomas Gerke, Duesseldorf (DE); Christian Kropf, Hilden (DE); Ursula Huchel, Cologne (DE); Axel Griesbeck, Cologne (DE); Agnieszka Landes, Bergheim (DE)

(73) Assignee: Henkel AG & Co., KGaA (DE)

( * ) Notice: Subject to any disclaimer, the term of this patent is extended or adjusted under 35 U.S.C. 154(b) by 0 days.

(21) Appl. No.: 15/247,694

(22) Filed: Aug. 25, 2016

(65) Prior Publication Data

US 2016/0362356 A1 Dec. 15, 2016

Related U.S. Application Data

(63) Continuation of application No. PCT/EP2015/055477, filed on Mar. 17, 2015.

(30) Foreign Application Priority Data

Mar. 24, 2014 (DE) .................. 10 2014 205 390

(51) Int. Cl.
| | | |
|---|---|---|
| *A61K 8/35* | (2006.01) | |
| *C07C 49/84* | (2006.01) | |
| *A61Q 13/00* | (2006.01) | |
| *C11D 3/20* | (2006.01) | |
| *C11D 3/50* | (2006.01) | |
| *C11D 9/00* | (2006.01) | |
| *C11B 9/00* | (2006.01) | |

(52) U.S. Cl.
CPC ............... *C07C 49/84* (2013.01); *A61K 8/35* (2013.01); *A61Q 13/00* (2013.01); *C11B 9/0061* (2013.01); *C11D 3/2072* (2013.01); *C11D 3/50* (2013.01); *A61K 2800/10* (2013.01); *A61K 2800/57* (2013.01); *A61K 2800/81* (2013.01); *C07C 2601/16* (2017.05)

(58) Field of Classification Search
CPC .......... A61K 8/35; A61Q 13/00; C07C 49/84; C11D 3/20; C11D 3/50; C11D 9/00
See application file for complete search history.

(56) References Cited

U.S. PATENT DOCUMENTS

| | | |
|---|---|---|
| 6,949,680 B2 | 9/2005 | Herrmann |
| 8,129,569 B2 | 3/2012 | Huchel et al. |
| 8,604,250 B2 | 12/2013 | Gerke et al. |

FOREIGN PATENT DOCUMENTS

CN 101921184 A 12/2010

OTHER PUBLICATIONS

PCT International Search Report (PCT/EP2015/055477) dated May 19, 2015.
Setsuo et al., "Preparation of Polyesters and Polyanhydrides from Vanillin", XP009184313, Kogyo Kagazu Zasshi, vol. 61, pp. 1097-1099, 1959.

*Primary Examiner* — Zohreh A Fay
(74) *Attorney, Agent, or Firm* — P. Scott Smith

(57) ABSTRACT

The invention relates to specific ketones of formula (I) which act as photolabile pro-fragrances. The invention also relates to detergents or cleaning agents, cosmetic agents and air fresheners including such ketones. The invention further relates to a method for creating a long-lasting fragrance on surfaces and also to a method for creating a long-lasting fragrance in a room using the aforementioned ketones.

10 Claims, No Drawings

PHOTOLABILE PRO-FRAGRANCES

FIELD OF THE INVENTION

The present invention generally relates to pro-fragrances, as they are used, for example, in the sector of detergents or cleaning agents, cosmetic agents, or air fresheners. The invention relates in particular to special ketones that function as photolabile pro-fragrances. The present invention further relates to detergents or cleaning agents, cosmetic agents, and air fresheners that include such ketones. It relates further to a method for long-lasting scenting of surfaces, and also to a method for long-lasting room scenting.

BACKGROUND OF THE INVENTION

Detergents or cleaning agents or cosmetic agents mostly include scents that impart a pleasant odor to the agents. The scents in most cases mask the odor of the other ingredients, producing a positive odor impression on the consumer.

In the detergent sector in particular, scents are important components of the composition, because the laundry should have a pleasant and, if possible, also fresh smell both when wet and when dry. A fundamental problem faced in the use of scents is that these are more or less readily volatile substances, but that a long-lasting scent effect is nevertheless desirable. The desired persistence of the scent impression can barely be achieved especially with fragrances that represent fresh and light notes of perfume and evaporate particularly quickly because of their high vapor pressure.

Delayed scent release can occur, e.g., thanks to carrier-bound use of scents. A carrier-bound precursor form of a scent is also known as a "pro-fragrance" or scent storage substance. A possibility for the delayed release of scents is the use of so-called photoactivatable substances as pro-fragrances. The action of sunlight or another electromagnetic radiation source of a specific wavelength induces the breakage of a covalent bond in the pro-fragrance molecule, thereby releasing a scent.

U.S. Pat. No. 6,949,680 discloses the use of specific phenyl ketones or pyridyl ketones as photoactivatable substances that, in a photochemical fragmentation, release a terminal alkene as an active substance in the presence of light. The aforesaid active substance possesses, for example, a scent-imparting or antimicrobial activity that is first delayed by the photochemically induced decomposition and is released on a specific surface over a longer period of time.

WO 2009/118219 A1 discloses photoactivatable substances that enable the release of cyclic terpenes or cyclic terpenoids.

WO 2011/101180 discloses the use of specific ketones as photoactivatable substances that release an active substance in a photochemical fragmentation in the presence of light. Said active substance possesses, for example, a scent-imparting that is first delayed by the photochemically induced decomposition, and is released on a specific surface over a longer period of time.

The object of the present invention was to provide photoactivatable substances as pro-fragrances, which permit the delayed release of fragrance ketones, in particular various damascones.

Furthermore, other desirable features and characteristics of the present invention will become apparent from the subsequent detailed description of the invention and the appended claims, taken in conjunction with this background of the invention.

BRIEF SUMMARY OF THE INVENTION

A compound of the general formula (I),

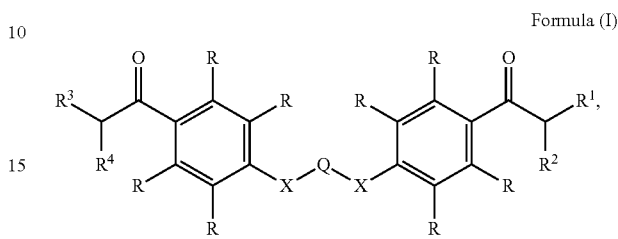

Formula (I)

where each R independently of one another stands for hydrogen, a halogen atom, an amino group, —$NO_2$, —NH-alkyl, —N(alkyl)$_2$, a linear or branched, substituted or unsubstituted alkoxy group having 1 to 15 C atoms or a linear or branched, substituted or unsubstituted alkyl group having 1 to 15 C atoms, a cycloalkyl group, a cycloalkenyl group, an acyl group, an aryl group, —OH, —COY— group, or a quaternary ammonium group of the formula (II)

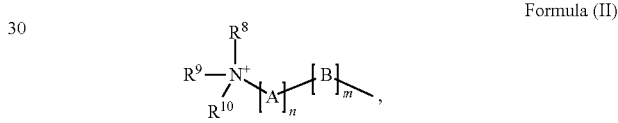

Formula (II)

R1 and R4 independently of one another stand for a substituted hydrocarbon group, which has at least one C=O group or an ester group, preferably a C=O group; R2 and R3 independently of one another stand for hydrogen, linear or branched, substituted or unsubstituted alkyl, preferably having 1-20 C atoms, linear or branched, substituted or unsubstituted alkenyl, preferably having 2-20 C atoms, substituted or unsubstituted aryl, preferably having 5-20 C atoms, alkylaryl, or arylalkyl, where all of the aforesaid groups can contain heteroatoms, preferably oxygen, sulfur, and nitrogen or can bear these as substituents; each X stands for a heteroatom, preferably oxygen or —NH—, —N(alkyl)-, —N(alkenyl)-, —N(aryl)-; Q stands for a group having 1 to 60 atoms, which independently of one another are selected from carbon, oxygen, silicon, nitrogen, or hydrogen where Q can be branched or linear or component of a ring; where heteroatoms in the bridge —X-Q-X— are not directly linked to one another and the bridge —X-Q-X— can stand for a heterocycle with at least two heteroatoms; Y stands for hydrogen, alkyl, cycloalkyl, aryl, acyl, —OH, —Oalkyl, —$NH_2$, NH-alkyl, —N(alkyl)$_2$, or halogen; A stands for a $CH_2$— or a $CH_2CH_2O$ group with n=1 to 20; B stands for oxygen with m=0 or 1, where m=0 when A is a $CH_2CH_2O$ group; and R8, R9, R10 each independently of one another stand for H or a substituted or unsubstituted alkyl, cycloalkyl, alkenyl, aryl, or acyl group-containing moiety and where in each case two of the groups R8, R9, R10 can be connected to one another by ring closure.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The object of the present invention was achieved by a compound of the general formula (I)

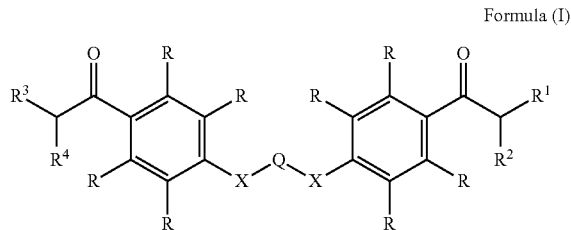

Formula (I)

where
each R independently of one another stands for hydrogen, a halogen atom, an amino group, $-NO_2$, —NH-alkyl, $-N(alkyl)_2$, a linear or branched, substituted or unsubstituted alkoxy group having 1 to 15 C atoms or a linear or branched, substituted or unsubstituted alkyl group having 1 to 15 C atoms, a cycloalkyl group, a cycloalkenyl group, an acyl group, an aryl group, —OH, —COY— group, or a quaternary ammonium group of the formula (II)

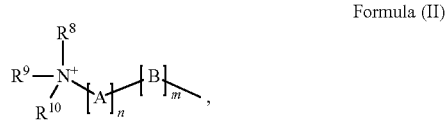

Formula (II)

R1 and R4 independently of one another stand for a substituted hydrocarbon group, which has at least one C=O group or at least one ester group, preferably a C=O group; R2 and R3 independently of one another stand for hydrogen, linear or branched, substituted or unsubstituted alkyl, preferably having 1-20 C atoms, linear or branched, substituted or unsubstituted alkenyl, preferably having 2-20 C atoms, substituted or unsubstituted aryl, preferably having 5-20 C atoms, alkylaryl, arylalkyl or —COY, where all of the aforesaid groups can contain heteroatoms, preferably oxygen, sulfur, and nitrogen or can bear these as substituents;
each X stands for a heteroatom, preferably oxygen or —NH—, —N(alkyl)-, —N(alkenyl)-, —N(aryl)-;
Q stands for a group having 1 to 60 atoms, which independently of one another are selected from carbon, oxygen, silicon, nitrogen, or hydrogen, where Q can be branched or linear or a component of a ring,
where heteroatoms in the bridge —X-Q-X— are not directly linked to one another and the bridge —X-Q-X— can stand for a heterocycle with at least two heteroatoms;
Y stands for hydrogen, alkyl, cycloalkyl, aryl, acyl, —OH,—Oalkyl, $-NH_2$, NH-alkyl, $-N(alkyl)_2$, or halogen;
A stands for a $CH_2$— or a $CH_2CH_2O$ group with n=1 to 20;
B stands for oxygen with m=0 or 1, where m=0 when A is a $CH_2CH_2O$ group;
R8, R9, R10 each independently of one another stand for H or a substituted or unsubstituted alkyl, cycloalkyl, alkenyl, aryl, or acyl group-containing moiety and where in each case two of the groups R8, R9, R10 can be connected to one another by ring closure.

It has been found surprisingly that the ketones of the invention are particularly effective pro-fragrances that permit the delayed release of fragrance ketones, in particular various damascones. Further, the increase in the molecular weight of pro-fragrances, compared with those in the prior art, leads to a further reduction in volatility. Use of the ketones of the invention in washing, cleaning, or care-providing agents resulted, in the context of their utilization, in an improved long-term scent effect, in particular in conjunction with textile treatment. For example, it was possible to observe an improved long-term scent effect in the treated laundry with the use of ketones of the invention in a laundry treatment agent, for example, a detergent and a fabric softener. In addition, corresponding products exhibit a particularly good shelf stability. The agents of the invention further make it possible to reduce the total quantity of perfume included in the agent, but nevertheless to achieve odor advantages on the washed textiles, in particular with regard to perceived freshness.

The ketone of the invention in accordance with the general formula (I) is suitable as a pro-fragrance for all usual alpha,beta-unsaturated fragrance ketones, selected in particular from isojasmone; musk indanone (6,7-dihydro-1,1,2,3,3-pentamethyl-4(5H)-indanone); alpha-damascone, beta-damascone, delta-damascone, gamma-damascone, damascenone, damarose, carvone, alpha-ionone, beta-ionone, gamma-methyl (so-called) ionone, dihydrojasmone, cis-jasmone, methylcedrenyl ketone or methylcedrylone, celery ketone or livescone, gelsone, hexalone, neobutenone, tetrameran, or mixtures thereof. The stored ketones can be released by the action of light comprising the wavelengths of 200 to 600 nm.

According to a preferred embodiment, X stands for oxygen and/or Q for a linear or branched, substituted or unsubstituted alkyl having 1 to 20 C atoms, preferably 1 to 4 C atoms, in particular for ethyl.

According to further preferred embodiments, in the compound according to formula (I):
(i) all R are hydrogen; and/or
(ii) R2 and R3 each independently stand for a linear or branched alkyl having 1 to 20 C atoms, preferably having 1 to 3 C atoms, particularly preferably for methyl, or for —COZ—, where Z stands for H, —R', —OR', —NR'R", —SR', or halogen, preferably —OR', and R' and R" independently of one another stand for hydrogen, a linear or branched, substituted or unsubstituted alkyl, aryl, alkylaryl, arylalkyl, or alkenyl group, all of which may contain optionally heteroatoms, preferably 1-3 heteroatoms selected from N, O, and S; and/or
(iii) R1 and R4 each independently stand for —$CR^aR^b$, where $R^a$ stands for a substituted hydrocarbon group, preferably having 2 to 20 C atoms, which has at least one C=O group or at least one ester group, preferably a C=O group, and $R^b$ stands for hydrogen, a halogen atom, an aryl group, $-NO_2$, a linear or branched, substituted or unsubstituted alkoxy group having 1 to 15 C atoms or a linear or branched, substituted or unsubstituted alkenyl group having 2 to 15 C atoms or a linear or branched, substituted or unsubstituted alkyl group having 1 to 15 C atoms or a substituted or unsubstituted aryl group.

Carbonyl compounds of the general formulas —(C=O)—Y— and —(C=O)—Z— are understood as —COY— and —COZ— groups in the context of the present application, where the groups —Y— and —Z— are defined as described above.

In various embodiments, the embodiments (i), (ii), and (iii) described above are combined.

In a further preferred embodiment of the invention, the R1 and R4 groups of the general formula (I) can stand for different substituted hydrocarbon groups, each of which independently of one another has at least one C=O group or at least one ester group, preferably a C=O-group. The R1 group of the formula (I) can be selected, for example, so that during its light-induced release, delta-damascone is released and the R4 group of the formula (I) can be selected concurrently so that an alpha,beta-unsaturated fragrance ketone different from delta-damascone is released. If the R1 and R4 groups are selected asymmetrically, so that different scents can be released, a preferred embodiment of the invention is present, because during use of such scent precursor compounds in washing, cleaning, or care-providing agents or cosmetic agents an improved long-term scent effect of more complex scent mixtures can be achieved, which is perceived as especially advantageous by the consumer.

In still further embodiments, the compound of the general formula (I) corresponds to the compound of the general formula (III)

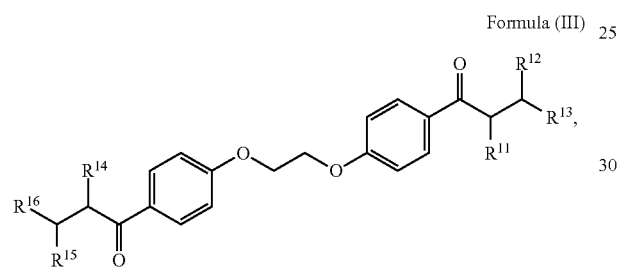

Formula (III)

where

R11 and R14 independently of one another stand for a linear or branched alkyl having 1 to 20 C atoms, preferably having 1 to 3 C atoms, particularly preferably for methyl, or for —COT, where T stands for H, —R5, —OR5, —NR5R6, —SR5, or halogen, preferably —OR5, and R5 and R6 independently of one another stand for hydrogen, a linear or branched, substituted or unsubstituted alkyl, aryl, alkylaryl, arylalkyl, or alkenyl group, all of which can contain optionally heteroatoms, preferably 1 to 3 heteroatoms, selected from N, O, and S;

R12 and R15 independently of one another stand for hydrogen, a halogen atom, an aryl group, —NO$_2$, a linear or branched, substituted or unsubstituted alkoxy group having 1 to 15 C atoms or a linear or branched, substituted or unsubstituted alkenyl group having 1 to 15 C atoms or a linear or branched, substituted or unsubstituted alkyl group having 1 to 15 C atoms or a substituted or unsubstituted aryl group, preferably for methyl;

R13 and R16 independently of one another stand for a substituted alkyl group having 2 to 20 C atoms, which has at least one C=O group or an ester group, preferably a C=O group, and which comprises in particular a cyclic, optionally substituted hydrocarbon group, preferably a cyclic, substituted alkenyl group, and where R13 and R16 stand in particular for

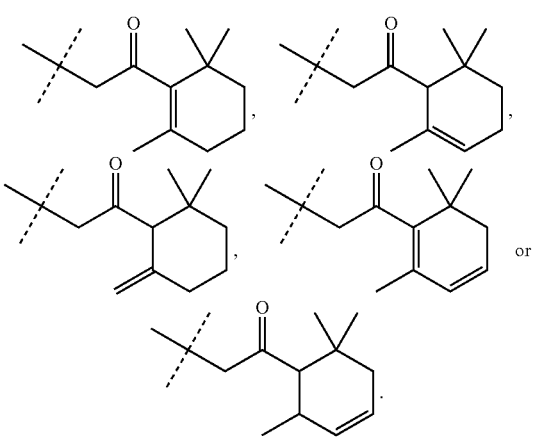

In various embodiments, alkyl in the definition of T and in the groups alkylaryl, arylalkyl, —Oalkyl, —NH-alkyl, and —N(alkyl)$_2$ stands for a linear or branched, substituted or unsubstituted alkyl group, preferably having 1 to 15 C atoms. Cycloalkyl stands for corresponding cyclic alkyl groups, preferably having 3 to 15 C atoms. Aryl preferably stands for a substituted or unsubstituted aryl group, preferably C6-C14 aryl, where optionally one or more of the ring C atoms can be replaced by heteroatoms such as O, S, or N and thus form a heteroaryl group. Acyl preferably stands for —C(O)alkyl, where alkyl is defined as above. In the alkylaryl and arylalkyl groups, aryl and alkyl are each as defined above. Halogen comprises fluorine, chlorine, bromine, and iodine, and is preferably fluorine, chlorine, or bromine, especially fluorine and chlorine.

(VIII):

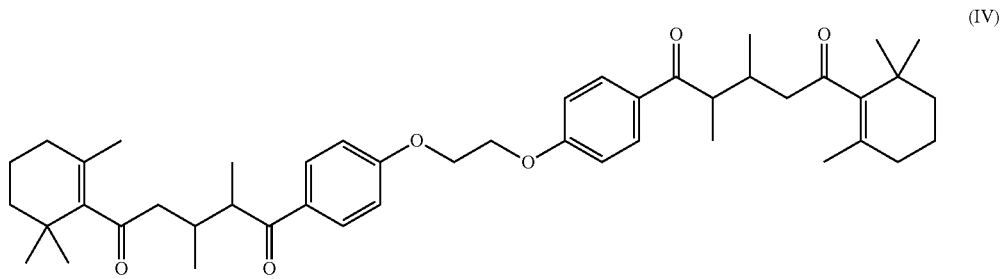

(IV)

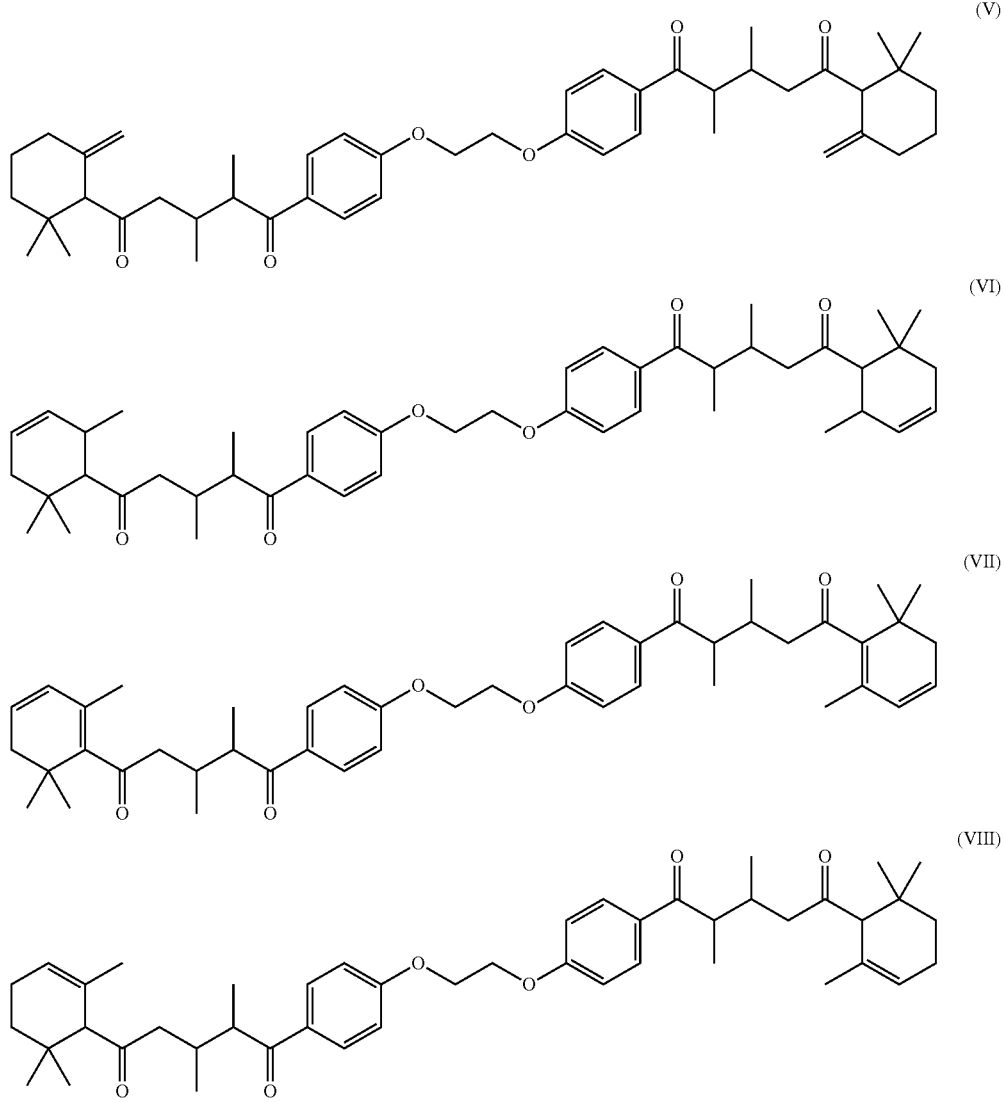

The ketones of the invention can be incorporated in stable fashion into the usual washing- or cleaning-agent matrices, into cosmetics and existing fragrance compositions. They enable delayed release of the stored scents, namely of damascones in the alpha, beta, gamma, or delta form, and of damascenones, in particular delta-damascenones. These ketones impart a particularly long-lasting fresh impression to usual detergents or cleaning agents and cosmetics. The dried, washed textile profits in particular from the good long-term fresh scent effect. Slow release of the stored fragrance occurs after the action of light (electromagnetic radiation) comprising the wavelengths of 200 to 600 nm.

A further subject of the present invention is a detergent or cleaning agent, preferably a detergent, fabric softener, or washing additive, containing at least one ketone according to the invention, said ketone being present preferably in amounts between 0.0001 and 5% by weight, advantageously between 0.001 and 4% by weight, more advantageously between 0.01 and 3% by weight, in particular between 0.1 and 2% by weight, based in each case on the total agent. Suitable cleaning agents are, e.g., cleaning agents for hard surfaces, such as preferably dishwashing agents. The cleaning agents can also be, e.g., household cleaners, all-purpose cleaners, window cleaners, floor cleaners, etc. The product can preferably be one for cleaning toilet bowls and urinals, advantageously a toilet flush cleaner for hanging in the toilet bowl.

According to a preferred embodiment of the invention, the detergent and/or cleaning agent of the invention includes at least one surfactant, selected from anionic, cationic, nonionic, zwitterionic, amphoteric surfactants, or mixtures thereof.

According to a further preferred embodiment of the invention, the agent of the invention is present in solid or liquid form.

A further subject of the invention is a cosmetic agent containing at least one ketone according to formula (I), said agent containing said ketone preferably in amounts between 0.0001 and 5% by weight, advantageously between 0.001 and 4% by weight, more advantageously between 0.01 and 3% by weight, in particular between 0.1 and 2% by weight, based in each case on the total agent.

A further subject of the invention is an air freshener (e.g., room air freshener, room deodorant, room spray, etc.) containing at least one ketone according to one of formulas (I) to (VIII), said ketone being present preferably in amounts between 0.0001 and 50% by weight, advantageously between 0.001 and 5% by weight, more advantageously between 0.1 and 3% by weight, in particular between 0.1 and 2% by weight, based in each case on the total agent.

According to a further preferred embodiment of the invention, additional scents are included in an agent of the invention (i.e., detergent or cleaning agent, cosmetic agent, or air freshener), selected in particular from the group comprising scents of natural or synthetic origin, preferably more readily volatile scents, higher-boiling scents, solid scents, and/or adherent scents.

Adherent fragrances that are usable with advantage in the context of the present invention are, for example, essential oils such as angelica oil, anise oil, arnica flower oil, basil oil, bay oil, bergamot oil, champaca flower oil, silver fir oil, silver fir cone oil, elemi oil, eucalyptus oil, fennel oil, fir needle oil, galbanum oil, geranium oil, gingergrass oil, guaiac wood oil, balsam gurjun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, curled peppermint oil, caraway oil, cumin oil, lavender oil, lemon grass oil, lime oil, tangerine oil, lemon balm oil, ambrette seed oil, myrrh oil, clove oil, neroli oil, niaouli oil, olibanum oil, orange oil, oregano oil, palmarosa oil, patchouli oil, balsam peru oil, petitgrain oil, pepper oil, peppermint oil, pimento oil, pine oil, rose oil, rosemary oil, sandalwood oil, celery oil, spike lavender oil, star anise oil, turpentine oil, thuja oil, thyme oil, verbena oil, vetiver oil, juniper berry oil, wormwood oil, wintergreen oil, ylang-ylang oil, ysop oil, cinnamon oil, cinnamon leaf oil, citronella oil, lemon oil, and cypress oil.

Higher-boiling or solid fragrances of natural or synthetic origin can, however, also be used in the context of the present invention as adherent fragrances or fragrance mixtures, therefore scents. These compounds include the compounds recited below, as well as mixtures thereof: ambrettolide, alpha-amylcinnamaldehyde, anethole, anisaldehyde, anise alcohol, anisole, anthranilic acid methyl ester, acetophenone, benzyl acetone, benzaldehyde, benzoic acid ethyl ester, benzophenone, benzyl alcohol, benzyl acetate, benzyl benzoate, benzyl formate, benzyl valerate, borneol, bornyl acetate, alpha-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl-n-amyl ketone, methylanthranilic acid methyl ester, p-methylacetophenone, methylchavicol, p-methylquinoline, methyl-beta-naphthyl ketone, methyl-n-nonylacetaldehyde, methyl-n-nonyl ketone, muscone, beta-naphthol ethyl ether, beta-naphthol methyl ether, nerol, nitrobenzene, n-nonylaldehyde, nonyl alcohol, n-octylaldehyde, p-oxyacetophenone, pentadecanolide, beta-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, gamma-undelactone, vanillin, veratraldehyde, cinnamaldehyde, cinnamyl alcohol, cinnamic acid, cinnamic acid ethyl ester, and cinnamic acid benzyl ester.

The more readily volatile scents include, in particular, the lower-boiling fragrances of natural or synthetic origin, which can be used alone or in mixtures. Examples of more readily volatile scents are alkylisothiocyanates (alkyl mustard oils), butanedione, limonene, linalool, linalyl acetate and propionate, menthol, menthone, methyl-n-heptenone, phellandrene, phenylacetaldehyde, terpinyl acetate, citral, and citronellal.

According to a further preferred embodiment, the agent of the invention (i.e., detergent or cleaning agent, cosmetic agent, or air freshener) has at least one, preferably multiple, active components, in particular cosmetic components or components having washing, care-providing, or cleaning activity, advantageously selected from the group comprising anionic surfactants, cationic surfactants, amphoteric surfactants, nonionic surfactants, acidifying agents, alkalizing agents, anti-creasing compounds, antibacterial substances, antioxidants, antiredeposition agents, antistatic agents, builder substances, bleaching agents, bleach activators, bleach stabilizers, bleach catalysts, ironing aids, cobuilders, scents, sanforizing agents, electrolytes, enzymes, color protectants, coloring agents, dyes, color transfer inhibitors, fluorescent agents, fungicides, germicides, odor-complexing substances, adjuvants, hydrotropes, rinse aids, complexing agents, preservatives, corrosion inhibitors, water-miscible organic solvents, optical brighteners, perfumes, perfume carriers, luster agents, pH adjusting agents, hydrophobizing and impregnating agents, polymers, swelling and anti-slip agents, foam inhibitors, phyllosilicates, dirt-repelling substances, silver protectants, silicone oils, soil release active substances, UV protection substances, viscosity regulators, thickeners, discoloration inhibitors, graying inhibitors, vitamins, and/or fabric softeners. For purposes of this invention, quantities for the agent of the invention in % by weight refer, unless otherwise stated, to the total weight of the agent of the invention.

The amounts of the individual ingredients in the agents of the invention (i.e., detergent or cleaning agent, cosmetic agent, or air freshener) are aimed in each case toward the intended use of the relevant agent, and the skilled artisan is familiar in principle with the orders of magnitude of the amounts of ingredients to be used, or can gather them from the relevant technical literature. The surfactant content, for example, will be selected to be higher or lower depending on the intended use of the agents of the invention. For example, the surfactant content of, e.g., detergents can usually be between 10 and 50% by weight, preferably between 12.5 and 30% by weight, and in particular between 15 and 25% by weight, whereas, e.g., cleaning agents for automatic dishwashing can include, e.g., between 0.1 and 10% by weight, preferably between 0.5 and 7.5% by weight, and in particular between 1 and 5% by weight of surfactants.

The agents of the invention (i.e., detergent or cleaning agent, cosmetic agent, or air freshener) can include surfactants; anionic surfactants, nonionic surfactants, and mixtures thereof, but also cationic surfactants are preferably appropriate. Suitable nonionic surfactants are, in particular, ethoxylation and/or propoxylation products of alkyl glycosides and/or of linear or branched alcohols each having 12 to 18 C atoms in the alkyl portion and 3 to 20, preferably 4 to 10, alkyl ether groups. Also usable are corresponding ethoxylation and/or propoxylation products of N-alkylamines, vicinal diols, fatty acid esters and fatty acid amides that correspond, in terms of the alkyl portion, to the aforesaid long-chain alcohol derivatives, and of alkylphenols having 5 to 12 C atoms in the alkyl group.

Suitable anionic surfactants are, in particular, soaps and those that contain sulfate or sulfonate groups having preferably alkali ions as cations. Usable soaps are preferably the alkali salts of the saturated or unsaturated fatty acids having 12 to 18 C atoms. Such fatty acids can also be used in incompletely neutralized form. The usable surfactants of the sulfate type include the salts of the sulfuric acid half-esters of fatty alcohols having 12 to 18 C atoms, and the sulfation products of the aforesaid nonionic surfactants having a low degree of ethoxylation. Included among the usable surfactants of the sulfonate type are linear alkylbenzenesulfonates having 9 to 14 C atoms in the alkyl portion, alkane sulfonates having 12 to 18 C atoms, and olefin sulfonates having 12 to 18 C atoms that arise upon reaction of corresponding monoolefins with sulfur trioxide, as well as alpha-sulfofatty acid esters that arise upon sulfonation of fatty acid methyl or ethyl esters.

Cationic surfactants are preferably selected from among the esterquats and/or the quaternary ammonium compounds (QACs) in accordance with the general formula $(R^{I})(R^{II})(R^{III})(R^{IV})N^{+}X^{-}$, in which $R^{I}$ to $R^{IV}$ stand for identical or different $C_{1-22}$ alkyl groups, $C_{7-28}$ aralkyl groups, or heterocyclic groups, such that two (or in the case of an aromatic bond such as in pyridine, even three) groups, together with the nitrogen atom, form the heterocycle (e.g., a pyridinium or imidazolinium compound), and $X^{-}$ denotes halide ions, sulfate ions, hydroxide ions, or similar anions. QACs can be prepared by reacting tertiary amines with alkylating agents such as, e.g., methyl chloride, benzyl chloride, dimethyl sulfate, dodecyl bromide, but ethylene oxide as well. The alkylation of tertiary amines having a long alkyl group and two methyl groups can be achieved particularly easily, and the quaternization of tertiary amines having two long groups and one methyl group can also be carried out using methyl chloride under mild conditions. Amines that possess three long alkyl groups or hydroxy-substituted alkyl groups have a low reactivity, and are quaternized, e.g., using dimethyl sulfate. Suitable QACs are, for example, benzalkonium chloride (N-alkyl-N,N-dimethylbenzylammonium chloride), benzalkon B (m,p-dichlorobenzyldimethyl-$C_{12}$-alkylammonium chloride), benzoxonium chloride (benzyldodecyl-bis(2-hydroxyethyl)ammonium chloride), cetrimonium bromide (N-hexadecyl-N,N-trimethylammonium bromide), benzetonium chloride (N,N-dimethyl-N-[2-[2-[p-(1,1,3,3-tetramethylbutyl)phenoxy]ethoxy]ethyl]benzylammonium chloride), dialkyldimethylammonium chlorides such as di-n-decyldimethylammonium chloride, didecyldimethylammonium bromide, dioctyldimethylammonium chloride, 1-cetylpyridinium chloride, and thiazoline iodide, as well as mixtures thereof. Preferred QACs are the benzalkonium chlorides having $C_{8}$ to $C_{22}$ alkyl groups, in particular $C_{12}$ to $C_{14}$ alkylbenzyldimethylammonium chloride.

Preferred esterquats are methyl-N-(2-hydroxyethyl)-N,N-di(tallowacyloxyethyl)ammonium methosulfate, bis(palmitoyl)ethylhydroxyethylmethylammonium methosulfate, or methyl-N,N-bis(acyloxyethyl)-N-(2-hydroxyethyl)ammonium methosulfate. Commercial examples are the methylhydroxyalkyldialkoyloxyalkylammonium methosulfates marketed by the company Stepan under the Stepantex® trademark, or the products from the company BASF SE known under the trade name Dehyquart®, or the products from the manufacturer Evonik known under the name Rewoquat.

Surfactants are included in the agents of the invention (i.e., detergent or cleaning agent, cosmetic agent, or air freshener) in proportions preferably of 5% by weight to 50% by weight, in particular of 8% by weight to 30% by weight.

In laundry post-treatment agents in particular, preferably up to 30% by weight, in particular 5% by weight to 15% by weight of surfactants are used, among them preferably cationic surfactants at least in part.

An agent of the invention, in particular a detergent or cleaning agent, preferably includes at least one water-soluble and/or water-insoluble, organic and/or inorganic builder. Water-soluble organic builder substances include polycarboxylic acids, in particular citric acid and sugar acids, monomeric and polymeric aminopolycarboxylic acids, in particular methylglycinediacetic acid, nitrilotriacetic acid, and ethylenediaminetetraacetic acid, as well as polyaspartic acid, polyphosphonic acids, in particular aminotris(methylenephosphonic acid), ethylenediaminetetrakis (methylenephosphonic acid), and 1-hydroxyethane-1,1-diphosphonic acid, polymeric hydroxy compounds such as dextrin, as well as polymeric (poly)carboxylic acids, polymeric acrylic acids, methacrylic acids, maleic acids, and mixed polymers thereof, which can also contain, polymerized into them, small portions of polymerizable substances having no carboxylic acid functionality. Suitable (although less preferred) compounds of this class are copolymers of acrylic acid or methacrylic acid with vinyl ethers, such as vinyl methyl ethers, vinyl esters, ethylene, propylene, and styrene, in which the proportion of acid is at least 50% by weight. Especially for the production of liquid detergents, the organic builder substances can be used in the form of aqueous solutions, preferably in the form of 30- to 50-weight-percent aqueous solutions. All the aforesaid acids are used as a rule in the form of their water-soluble salts, in particular their alkali salts.

Organic builder substances can be included if desired in amounts of up to 40% by weight, in particular up to 25% by weight, and preferably of 1% by weight to 8% by weight. Amounts close to the aforesaid upper limit are used preferably in pasty or liquid, in particular water-containing, agents of the invention. Laundry post-treatment agents of the invention such as, e.g., fabric softeners, can also, if applicable, be free of organic builder.

Possible water-soluble inorganic builder materials are, in particular, alkali silicates and polyphosphates, preferably sodium triphosphate. Crystalline or amorphous alkali aluminosilicates can be used in particular as water-insoluble, water-dispersible inorganic builder materials, if desired, in amounts of up to 50% by weight, preferably not above 40% by weight, and in liquid agents in particular of 1% by weight to 5% by weight. Among these, the crystalline sodium aluminosilicates of detergent quality, in particular zeolite A, P, and if applicable X, are preferred. Amounts close to the aforesaid upper limit are used preferably in solid, particulate agents. Suitable aluminosilicates have in particular no particles with a particle size greater than 30 μm, and preferably are made up of at least 80% by weight of particles with a size less than 10 μm.

Suitable substitutes or partial substitutes for the aforesaid aluminosilicate are crystalline alkali silicates, which can be present alone or mixed with amorphous silicates. The alkali silicates usable in the agents of the invention as builders preferably have a molar ratio of alkali oxide to $SiO_2$ below 0.95, in particular of 1:1.1 to 1:12, and can be present in amorphous or crystalline fashion. Preferred alkali silicates are the sodium silicates, in particular amorphous sodium silicates, having a $Na_2O:SiO_2$ molar ratio of 1:2 to 1:2.8. Crystalline phyllosilicates of the general formula $Na_2Si_xO_{2x+1} \cdot yH_2O$, in which x, the so-called modulus, is a number from 1.9 to 4 and y is a number from 0 to 20, and preferred values for x are 2, 3, or 4, are preferred for use as crystalline silicates, which can be present alone or in a mixture with amorphous silicates. Preferred crystalline phyllosilicates are those in which x in the aforesaid general formula assumes the values 2 or 3. In particular, both beta- and delta-sodium disilicates ($Na_2Si_2O_5 \cdot yH_2O$) are preferred. Practically anhydrous crystalline alkali silicates prepared from amorphous alkali silicates and having the aforesaid general formula, in which x denotes a number from 1.9 to 2.1, can also be used in agents of the invention. In a further preferred embodiment of agents of the invention, a crystalline sodium phyllosilicate having a modulus of 2 to 3 can be used, such as the one that can be prepared from sand and soda. Crystalline sodium silicates having a modulus in the range of 1.9 to 3.5 are used in a further preferred embodiment of agents of the invention. If alkali aluminosilicate, in particular zeolite, is present as an additional builder substance, the weight ratio of aluminosilicate to silicate, based in each case on anhydrous active substances, is preferably 1:10 to 10:1. In agents that include both amorphous and crystalline alkali silicates, the weight ratio of amorphous alkali silicate to crystalline alkali silicate is preferably 1:2 to 2:1, and in particular 1:1 to 2:1.

Builder substances are included in the agents of the invention, if desired, preferably in amounts of up to 60% by weight, in particular of 5% by weight to 40% by weight. Laundry post-treatment agents of the invention such as, e.g., fabric softeners, of the invention are preferably free of inorganic builder.

Peroxygen compounds that are suitable are, in particular, organic peracids or peracid salts of organic acids such as phthalimidopercaproic acid, perbenzoic acid, or salts of diperdodecanedioic acid, hydrogen peroxide, and inorganic salts that release hydrogen peroxide under application conditions, such as perborate, percarbonate, and/or persilicate. If solid peroxygen compounds are to be used, they may be used in the form of powders or granules, which can also be encapsulated in a manner known in principle. Alkali percarbonate, alkali perborate monohydrate, or, in particular in liquid agents, hydrogen peroxide in the form of aqueous solutions including 3% by weight to 10% by weight of hydrogen peroxide, is optionally used especially preferably. If an agent of the invention includes bleaching agents, such as preferably peroxygen compounds, the latter are present in amounts of preferably up to 50% by weight, in particular of 5% by weight to 30% by weight. The addition of small amounts of known bleaching-agent stabilizers such as, for example, phosphonates, borates or metaborates, and metasilicates, as well as magnesium salts such as magnesium sulfate, may be useful.

Compounds that, under perhydrolysis conditions, afford aliphatic peroxocarboxylic acids having preferably 1 to 10 C atoms, in particular 2 to 4 C atoms, and/or optionally substituted perbenzoic acid, can be used as bleach activators. Substances that carry the O- and/or N-acyl groups having the aforesaid number of C atoms, and/or optionally substituted benzoyl groups, are suitable. Polyacylated alkylenediamines, in particular tetraacetylethylendiamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- or iso-NOBS), carboxylic acid anhydrides, in particular phthalic anhydride, acylated polyhydric alcohols, in particular triacetin, ethylene glycol diacetate, 2,5-diacetoxy-2,5-dihydrofuran, and enol esters, as well as acetylated sorbitol and mannitol, or mixtures thereof (SORMAN), acylated sugar derivatives, in particular pentaacetylglucose (PAG), pentaacetylfructose, tetraacetylxylose, and octaacetyllactose, as well as acetylated, optionally N-alkylated glucamine and gluconolactone, and/or N-acylated lactams, for example, N-benzoylcaprolactam, are preferred. Hydrophilically substituted acyl acetals and acyl lactams are likewise used with preference. Combinations of conventional bleach activators can also be used. Such bleach activators can be included in the usual quantitative range, preferably in amounts of 1% by weight to 10% by weight, in particular 2% by weight to 8% by weight, based on the total agent.

In addition to or instead of the aforementioned conventional bleach activators, sulfonimines and/or bleach-intensifying transition metal salts or transition metal complexes can also be included as so-called bleach catalysts.

Suitable enzymes usable in the agents are those from the class of the proteases, cutinases, amylases, pullulanases, hemicellulases, cellulases, lipases, oxidases, and peroxidases, as well as mixtures thereof. Enzymatic active substances obtained from fungi or bacteria, such as *Bacillus subtilis, Bacillus licheniformis, Streptomyces griseus, Humicola lanuginosa, Humicola insolens, Pseudomonas pseudoalcaligenes*, or *Pseudomonas cepacia* are especially suitable. The optionally employed enzymes may be adsorbed onto carrier substances and/or encapsulated in shell-forming substances to protect them from premature inactivation. They are included in the agents of the invention, if desired, preferably in amounts not above 5% by weight, in particular of 0.2% by weight to 2% by weight.

The agents can optionally include as optical brighteners, for example, derivatives of diaminostilbenedisulfonic acid or alkali metal salts thereof. Suitable, for example, are salts of 4,4'-bis(2-anilino-4-morpholino-1,3,5-triazinyl-6-amino) stilbene-2,2'-disulfonic acid, or compounds of similar structure that carry, instead of the morpholino group, a diethanolamino group, a methylamino group, an anilino group, or a 2-methoxyethylamino group.

Suitable foam inhibitors include, for example, organopolysiloxanes and mixtures thereof with microfine, optionally silanized silicic acid, as well as paraffin waxes and mixtures thereof with silanized silicic acid or bis-fatty acid alkylenediamides. Mixtures of different foam inhibitors, for example, those made of silicones, paraffins, or waxes, are also used with advantage. The foam inhibitors, in particular silicone- and/or paraffin-including foam inhibitors, are preferably bound to a granular carrier substance that is soluble or dispersible in water. Mixtures of paraffins and bistearylethylenediamides are particularly preferred in this context.

In addition, the agents can also contain components that positively influence the ability of oils and fats to be washed out of textiles, so-called soil release active substances. This effect becomes particularly apparent when a textile is stained that has already been previously washed repeatedly with an agent of the invention that includes this oil- and fat-releasing component. The preferred oil- and fat-releasing components include, for example, nonionic cellulose ethers such as methyl cellulose and methylhydroxypropyl cellulose having a 15 to 30% by weight proportion of methoxy groups and a 1 to 15% by weight proportion of hydroxypropoxy groups, based in each case on the nonionic cellulose ethers, as well as polymers, known from the prior art, of phthalic acid and/or terephthalic acid or of their derivatives with monomeric and/or polymeric diols, in particular polymers of ethylene terephthalates and/or polyethylene glycol terephthalates or anionically and/or nonionically modified derivatives thereof.

The agents can also include color transfer inhibitors, preferably in amounts of 0.1% by weight to 2% by weight, in particular 0.1% by weight to 1% by weight, which in a preferred embodiment of the invention are polymers of vinylpyrrolidone, vinylimidazole, vinylpyridine-N-oxide, or copolymers thereof.

Graying inhibitors have the task of keeping dirt that has been released from the textile fibers suspended in the bath. Water-soluble colloids of a mainly organic nature are suitable for this purpose, for example, starch, size, gelatin, salts of ether carboxylic or ether sulfonic acids of starch or of cellulose, or salts of acid sulfuric acid esters of cellulose or of starch. Water-soluble polyamides containing acid groups are also suitable for this purpose. Further, starch derivatives other than those stated above can also be used, for example, aldehyde starches. Cellulose ethers such as carboxymethylcellulose (sodium salt), methyl cellulose, hydroxyalkyl cellulose, and mixed ethers such as methyl hydroxyethyl cellulose, methyl hydroxypropyl cellulose, methyl carboxymethyl cellulose, and mixtures thereof can be used preferably, for example, in amounts of 0.1 to 5% by weight, based on the agents.

The organic solvents usable in the agents of the invention, especially when the latter exist in liquid or pasty form, are alcohols having 1 to 4 C atoms, in particular methanol, ethanol, isopropanol, and tert-butanol, diols having 2 to 4 C atoms, in particular ethylene glycol and propylene glycol, as well as mixtures thereof, and the ethers derivable from the aforesaid compound classes. Water-miscible solvents of this kind are present in the agents of the invention preferably in amounts not above 30% by weight, in particular of 6% by weight to 20% by weight.

In order to establish a desired pH that does not result of itself from mixture of the other components, the agents of the invention can include system-compatible and environmentally compatible acids, in particular citric acid, acetic acid, tartaric acid, malic acid, lactic acid, glycolic acid, succinic acid, glutaric acid, and/or adipic acid, but also mineral acids, in particular sulfuric acid, or bases, in particular ammonium hydroxides or alkali hydroxides. pH regulators of this kind are optionally included in the agents of the invention in amounts preferably not above 20% by weight, in particular of 1.2% by weight to 17% by weight.

The production of solid agents of the invention (i.e., in particular detergents or cleaning agents) presents no difficulties and can in principle occur in known fashion, for example, by spray-drying or granulation; an optional peroxygen compound and optional bleach catalyst can, if applicable, be added later. A method comprising an extrusion step is preferred for producing agents of the invention having an elevated bulk weight, in particular in the range of 650 g/L to 950 g/L. The production of liquid agents of the invention likewise presents no difficulties and can likewise occur in known fashion.

The preparation of the ketones of the invention is described in exemplifying fashion in the Examples section, with reference to the preparation of a pro-fragrance containing delta-damascones. The other ketones of the general formula (I), and in particular all ketones of formulas (IV) to (VIII), are also obtainable via this principle synthesis route. In the synthesis of ketones of the invention in which R1 and R4 are selected so that different alpha,beta-unsaturated fragrance ketones can be released from a ketone of the invention, mixtures of differently substituted and identically substituted ketones of the invention are obtained. The relation of the differently substituted and identically substituted ketones of the invention to one another is subject to the employed amount of substance for the individual fragrance ketones, on the one hand, and the natural statistics, on the other.

According to a preferred embodiment, the teaching of the invention can be used to significantly reduce the perfume proportion in washing, cleaning, and personal care agents. As a result, it is possible to offer perfumed products even for those particularly sensitive consumers who, because of specific intolerances and irritations, can use normally perfumed products only to a limited extent or not at all.

A preferred solid, in particular powdered, detergent of the invention can in particular also contain, apart from the ketone of the invention, components that are selected, e.g., from the following:

anionic surfactants such as, preferably, alkylbenzenesulfonate, alkyl sulfate, e.g., in amounts preferably of 5 to 30% by weight, nonionic surfactants such as, preferably, fatty alcohol polyglycol ethers, alkylpolyglucoside, fatty acid glucamide, e.g., in amounts preferably of 0.5 to 15% by weight, builders such as, e.g., zeolite, polycarboxylate, sodium citrate, in amounts of, e.g., 0 to 70% by weight, advantageously 5 to 60% by weight, preferably 10 to 55% by weight, in particular 15 to 40% by weight, alkalis such as, e.g., sodium carbonate, in amounts of, e.g., 0 to 35% by weight, advantageously 1 to 30% by weight, preferably 2 to 25% by weight, in particular 5 to 20% by weight, bleaching agents such as, e.g., sodium perborate, sodium percarbonate, in amounts of, e.g., 0 to 30% by weight, advantageously 5 to 25% by weight, preferably 10 to 20% by weight, corrosion inhibitors, e.g., sodium silicate, in amounts of, e.g., 0 to 10% by weight, advantageously 1 to 6% by weight, preferably 2 to 5% by weight, in particular 3 to 4% by weight, stabilizers, e.g., phosphonates, advantageously 0 to 1% by weight, foam inhibitor, e.g., soap, silicone oils, paraffins, advantageously 0 to 4% by weight, preferably 0.1 to 3% by weight, in particular 0.2 to 1% by weight, enzymes, e.g., proteases, amylases, cellulases, lipases, advantageously 0 to 2% by weight, preferably 0.2 to 1% by weight, in particular 0.3 to 0.8% by weight, graying inhibitor, e.g., carboxymethylcellulose, advantageously 0 to 1% by weight, discoloration inhibitor, e.g., polyvinylpyrrolidone derivatives, advantageously 0 to 2% by weight, adjusting agent, e.g., sodium sulfate, advantageously 0 to 20% by weight, optical brightener, e.g., stilbene derivative, biphenyl derivative, advantageously 0 to 0.4% by weight, in particular 0.1 to 0.3% by weight, optionally further fragrances, optionally water, optionally soap, optionally bleach activators, optionally cellulose derivatives, optionally dirt repellents, % by weight being based in each case on the total agent.

In a further preferred embodiment of the invention, the agent is present in liquid form, preferably in gel form. Preferred liquid detergents or cleaning agents, as well as cosmetics, have water contents of, e.g., 10 to 95% by weight, preferably 20 to 80% by weight, and in particular 30 to 70% by weight, based on the total agent. In the case of liquid concentrates, the water content can also be particularly low, e.g., <30% by weight, preferably <20% by weight, in particular <15% by weight, % by weight being based in each case on the total agent. The liquid agents can also include non-aqueous solvents.

A preferred liquid, in particular gel-like, detergent of the invention can in particular also include, apart from the ketone of the invention, components that are selected, e.g., from the following:

anionic surfactants such as preferably alkylbenzenesulfonate, alkyl sulfate, e.g., in amounts preferably of 5 to 40% by weight, nonionic surfactants such as, preferably, fatty alcohol polyglycol ethers, alkylpolyglucoside, fatty acid glucamide, e.g., in amounts, preferably, of 0.5 to 25% by weight, builders such as, e.g., zeolite, polycarboxylate, sodium citrate, advantageously 0 to 15% by weight, preferably 0.01 to 10% by weight, in particular 0.1 to 5% by weight, foam inhibitor, e.g., soap, silicone oils, paraffins, in amounts of, e.g., 0 to 10% by weight, advantageously 0.1 to 4% by weight, preferably 0.2 to 2% by weight, in particular 1 to 3% by weight, enzymes, e.g., proteases, amylases, cellulases, lipases, in amounts of, e.g., 0 to 3% by weight, advantageously 0.1 to 2% by weight, preferably 0.2 to 1% by weight, in particular 0.3 to 0.8% by weight, optical brightener, e.g., stilbene derivative, biphenyl derivative, in amounts of, e.g., 0 to 1% by weight, advantageously 0.1 to 0.30% by weight, in particular 0.1 to 0.4% by weight, optionally further fragrances, optionally stabilizers, water, optionally soap, in amounts of, e.g., 0 to 25% by weight, advantageously 1 to 20% by weight, preferably 2 to 15% by weight, in particular 5 to 10% by weight, optionally solvents (preferably alcohols), advantageously 0 to 25% by weight, preferably 1 to 20% by weight, in particular 2 to 15% by weight, % by weight being based in each case on the total agent.

A preferred liquid fabric softener of the invention can in particular also include, apart from the ketone of the invention, components that are selected from the following:

cationic surfactants such as especially esterquats, e.g., in amounts of 5 to 30% by weight, cosurfactants such as, e.g., glycerol monostearate, stearic acid, fatty alcohols, fatty alcohol ethoxylates, e.g., in amounts of 0 to 5% by weight, preferably 0.1 to 4% by weight, emulsifiers such as, e.g., fatty amine ethoxylates, e.g., in amounts of 0 to 4% by weight, preferably 0.1 to 3% by weight, optionally further scents, dyes, preferably in the ppm range, stabilizers, preferably in the ppm range, solvents such as, e.g., water, in amounts preferably of 60 to 90% by weight, % by weight being based in each case on the total agent.

A further subject of the invention is a cosmetic agent, the cosmetic agent including a ketone of the invention according to formula (I).

A further subject of the invention is a method for long-lasting scenting of surfaces, a ketone of the invention according to formula (I) or a detergent or cleaning agent, cosmetic agent, or air freshener of the invention being applied to the surface to be scented (e.g., textile, dishware, floor), and said surface then being exposed to electromagnetic radiation comprising the wavelengths of 200 to 600 nm.

A further subject of the invention is a method for long-lasting room scenting, an air freshener of the invention being exposed to electromagnetic radiation comprising the wavelengths of 200 to 600 nm.

EXAMPLE 1

Synthesis

Preparation of the Bridging Anchor Molecule (Step 1)

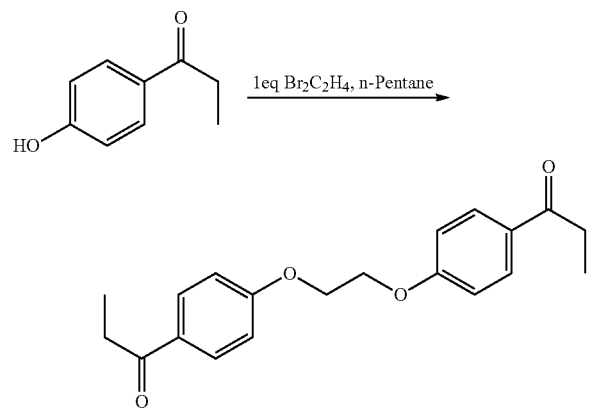

Under a protective gas atmosphere 3.05 g (22.02 mmol) of potassium carbonate and 1.10 g (7.34 mmol) of hydroxypropiophenone in 25 mL of n-pentane were charged into a 3-neck flask. 0.65 ml (7.5 mmol) of dibromoethane was added dropwise thereto and the mixture was heated to 110° C. with stirring. The reaction mixture was stirred overnight at this temperature. Next, the mixture was filtered through a glass frit (filled with Celite) and washed twice with acetone, and the solvent was removed at reduced pressure.

GC/MS: (25-320 M), m/z: 326, 297, 177, 163, 147, 134, 121, 104, 92, 77, 66, 57. $t_R$ (25-320M)=24.224

$^1$H NMR: (400 MHz, CDCl$_3$) δ (ppm)=7.88 (d, 4H); 6.91 (d, 4H); 4.35 (s, 4H); 2.90 (m, 4H); 1.17 (m, 6H).

Preparation of a Bridged Photocage

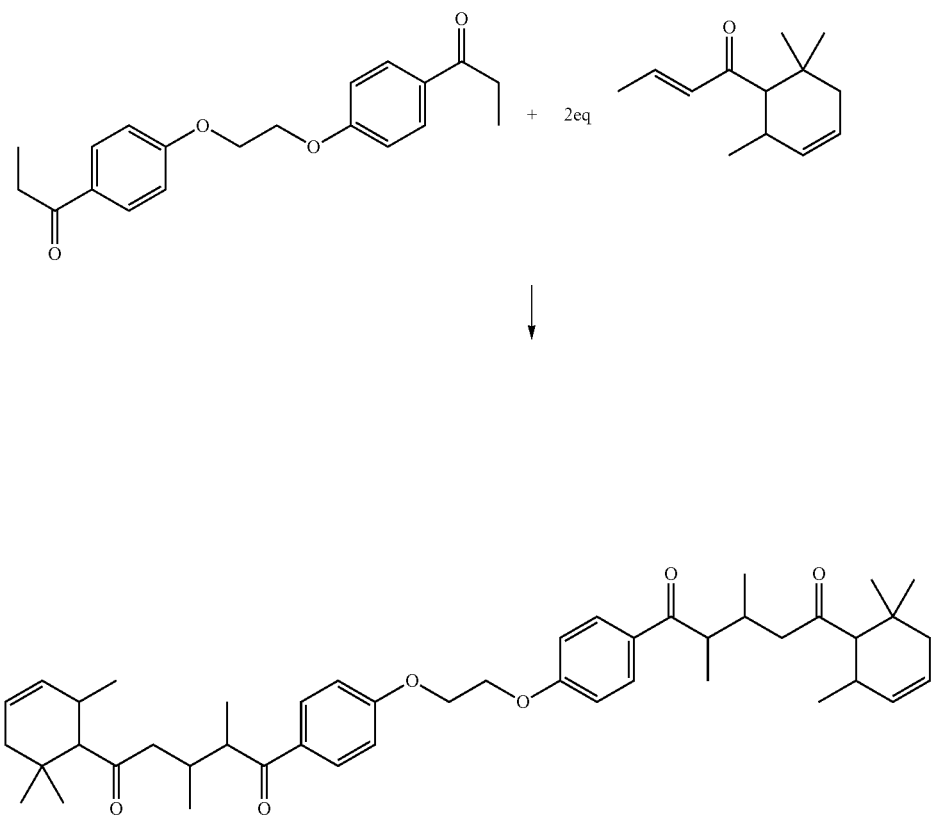

4.00 mmol of diisopropylamine in 4 mL of THF was charged under argon and cooled to −78° C. (dry ice/acetone bath) for 30 minutes. Then, 4.80 mmol of n-BuLi was added slowly dropwise and the mixture was stirred for 1 hour with cooling.

In a second flask, 2.00 mmol of the compound prepared in step 1 was dissolved in 15 mL of THF under argon and added using a syringe through a septum to the reaction mixture consisting of n-BuLi and diisopropylamine in THF. After 1 hour of stirring at −78° C., this was combined with 4.68 mmol of cerium(III) chloride; the mixture was stirred for 30 minutes, and then 4 mmol of damascone was added slowly dropwise. The mixture was stirred overnight and slowly heated to room temperature. Then, the mixture was extracted three times with diethyl ether; the pooled organic phases were washed with a saturated NaCl solution and dried over magnesium sulfate; and the solvent was removed under vacuum. An orange, viscous product was obtained in a 38% yield.

$^1$H NMR: (400 MHz, CDCl$_3$) δ (ppm)=7.88 (d, 4H); 6.91 (d, 4H); 5.5 (m, 4H); 3.80 (t, 4H); 2.50 (d, 4H); 2.2 (m, 4H); 1.80 (m, 4H); 1.1-0.8 (m, 34H).

EXAMPLE 2

Release Behavior

The test substances were incorporated in an equal number of moles in regard to the fragrance included therein into a fabric softener, and this was used in the rinse cycle of a common household washing process. The thus treated laundry after drying for x hours was exposed to sunlight and then assessed for odor by a panel of 10 individuals with olfactory training; the laundry was assessed by each panel member in two independent rounds. The scent intensity is expressed using a scale of 1 to 10 (10=very strong, 1=no scent). The values given in the table reflect the rounded arithmetic mean of all individual assessments.

The pure fragrance delta-damascone (reference) and the compound with the formula (IX), already known from the prior art, were tested in comparison with the ketone of the formula (IV) of the invention Formula IX

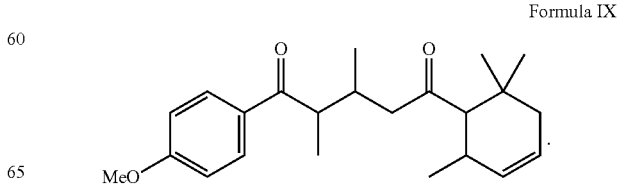

| Sample | Dosage [% by wt.] | Scent intensity after 1 h of sun | Scent intensity after 3 h of sun | Scent intensity after 5 h of sun | Scent intensity after 7 h of sun |
|---|---|---|---|---|---|
| Reference | 0.4 | 3 | 2 | 1 | 2 |
| Ketone IX | 0.74 | 3 | 3 | 3 | 3 |
| Ketone IV | 0.99 | 4 | 3 | 4 | 4 |

It is apparent that the compound of the invention is superior to the prior-art substances in regard to the long-term scent intensity.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A compound of the general formula (III)

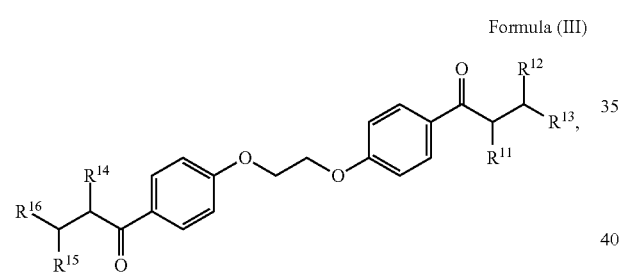

Formula (III)

where
R11 and R14 independently of one another stand for a linear or branched alkyl having 1 to 20 C atoms, and R5 and R6 independently of one another stand for hydrogen, a linear or branched, substituted or unsubstituted alkyl, aryl, alkylaryl, arylalkyl, or alkenyl group, all of which can contain optionally heteroatoms;

R12 and R15 independently of one another stand for hydrogen, a halogen atom, an aryl group, —NO$_2$, a linear or branched, substituted or unsubstituted alkoxy group having 1 to 15 C atoms or a linear or branched, substituted or unsubstituted alkenyl group having 1 to 15 C atoms or a linear or branched, substituted or unsubstituted alkyl group having 1 to 15 C atoms or a substituted or unsubstituted aryl group, R13 and R16 independently of one another stand for a substituted alkyl group having 2 to 20 C atoms, which has at least one C═O group or an ester group.

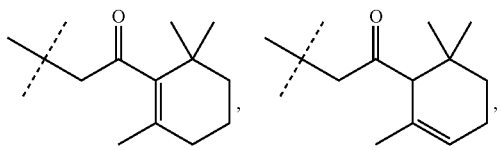

,

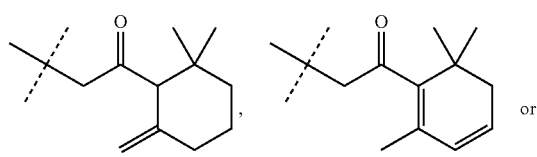

or

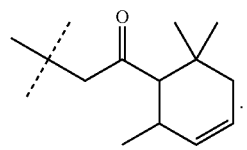

.

2. The compound according to claim 1, wherein the compound is selected from the group consisting of formulas (IV) to (VIII):

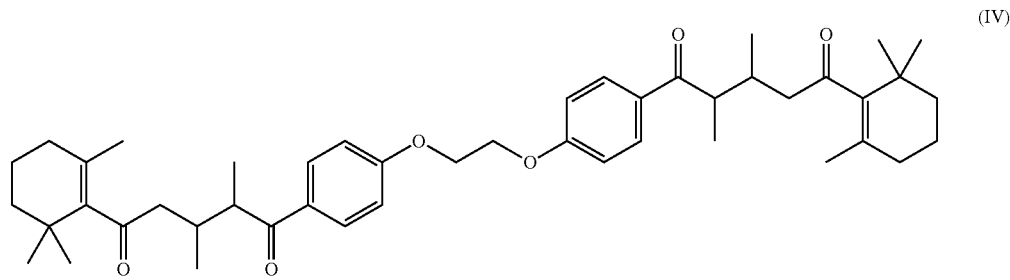

(IV)

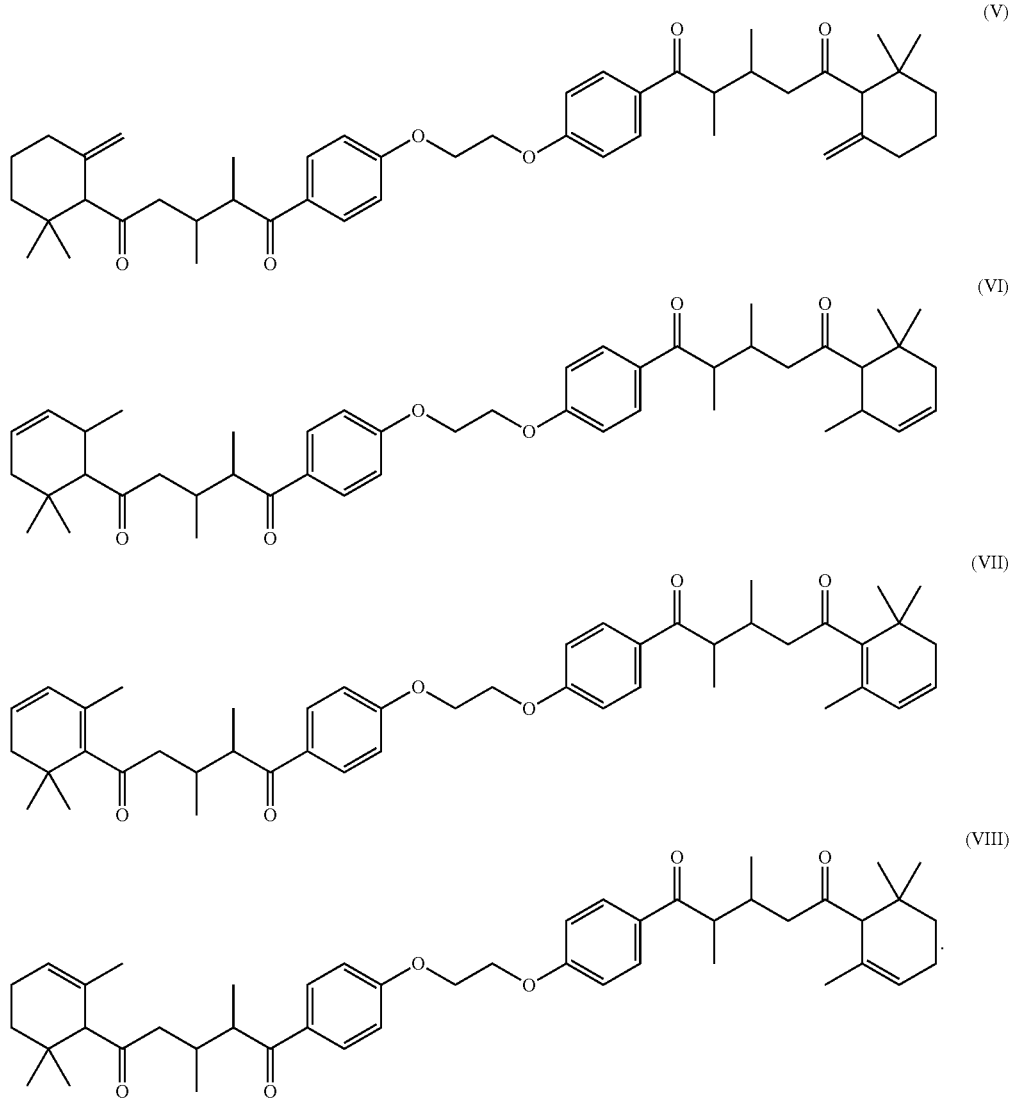

3. A detergent or cleaning agent, comprising at least one compound according to claim 1, wherein the compound is present in amounts of 0.0001 to 5% by weight, based on the total agent.

4. The detergent or cleaning agent of claim 3, wherein the compound comprises 0.01 to 3% by weight, based in each case on the total agent.

5. The detergent or cleaning agent according to claim 3, wherein the agent further comprises (1) at least one surfactant, selected from the group comprising anionic, cationic, nonionic, zwitterionic, amphoteric surfactants, or mixtures thereof; and/or (2) it is present in solid or liquid form.

6. An air freshener, comprising at compound of claim 1, wherein the cited compound is present in amounts of 0.0001 and 50% by weight based on the total agent.

7. The air freshener of claim 6, wherein the compound comprises 0.01 to 3% by weight, based on the total weight of the air freshener.

8. A cosmetic agent, comprising at least one compound according to claim 1, wherein the compound is present in amounts between 0.0001 and 5% by weight based on the total weight of the cosmetic agent.

9. A cosmetic agent according to claim 8, wherein the compound comprises 0.01 to 3% by weight based on the total weight of the cosmetic agent.

10. A method for the long-lasting scenting of surfaces, comprising applying to a surface to be scented at least one compound according to claim 1, and exposing the compound to electromagnetic radiation comprising the wavelengths of 200 to 600 nm.

* * * * *